US012622792B2

(12) United States Patent　　　　(10) Patent No.:　US 12,622,792 B2

Reyes　　　　　　　　　　　　　　　(45) Date of Patent:　　May 12, 2026

(54) PROSTHETIC WRIST

(71) Applicant: Manuel Reyes, Newport, RI (US)

(72) Inventor: Manuel Reyes, Newport, RI (US)

( * ) Notice: Subject to any disclaimer, the term of this patent is extended or adjusted under 35 U.S.C. 154(b) by 1342 days.

(21) Appl. No.: 17/305,536

(22) Filed: Jul. 9, 2021

(65) Prior Publication Data

US 2021/0330479 A1　　　Oct. 28, 2021

(51) Int. Cl.
　　A61F 2/58　　　　(2006.01)
　　A61F 2/68　　　　(2006.01)
　　A61F 2/50　　　　(2006.01)

(52) U.S. Cl.
　　CPC ...... A61F 2/585 (2013.01); *A61F 2002/5072* (2013.01); *A61F 2002/5083* (2013.01); *A61F 2002/6854* (2013.01)

(58) Field of Classification Search
　　CPC .... A61F 2/50; A61F 2/58; A61F 2/581; A61F 2/583; A61F 2/585; A61F 2/586; A61F 2/588
　　See application file for complete search history.

(56) References Cited

U.S. PATENT DOCUMENTS 2,457,316 A * 12/1948 Northrop ................ A61F 2/585
　　　　　　　　　　　　　　　　　　　　　　623/62
11,185,426 B2 * 11/2021 Gill ........................... A61F 2/54

* cited by examiner

*Primary Examiner* — Marcia L Watkins

(57) ABSTRACT

A prosthetic wrist for terminal devices preserves free rotation under high rotational or axial loads.

3 Claims, 5 Drawing Sheets

100

<u>100</u>

PROSTHETIC WRIST

This application is a continuation in part of application Ser. No. 16/029,925 filed 2018 Jul. 9.

TECHNICAL FIELD

The present disclosure relates to upper limb prosthetic devices used for maneuvering under load.

BACKGROUND

A prosthesis is any artificial device that replaces a body part. The fit of a prosthetic device accommodates the nature of the activity, the level of muscle strain, and user perspiration. Energy storage and return is a design consideration that affects the impact on the device and the response from the device to the impact. Utility, weight, and durability of the components affects the comfort and performance of a prosthesis.

A prosthetic socket is a customized prosthetic interface suspended to a residual limb of an amputee. Prosthetic sockets are typically semi-rigid, composite forms constructed with a number of components engaged along a central axis. These integrated components may include suspension methods, elbow, wrist, knee, and ankle units, and use-specific terminal devices.

Pronation and supination describe the rotation of the forearm to move the hand into a palm-up (pronation) or palm-down (supination) position. Internal and external rotation is the rotation of the arm at the shoulder or leg at the pelvis. Internal and external rotation at these joints rotates all of the distal extremities relative to the torso. Pronation, supination and internal and external rotation, whether intentional or unintentional, are important design considerations for prosthetic-limb devices.

A mechanical wrist unit is one of the distal components of an upper limb prosthetic socket. The wrist unit enables secure attachment, removal and re-attachment of various terminal devices. The wrist unit designs have two modes: free-rotation mode and rotation-locked mode. In locked mode, certain features allow specificity of angular positioning of the terminal device.

Current designs of mechanical wrist units have a tendency to bind under high rotational or axial load when in free-rotation mode.

A terminal device is a prosthetic device that enables various specialized tasks. The terminal device attaches to a mechanical wrist unit. Terminal devices typically have a threaded stud that threads into an adapter. The adapter is dependent on the design of the wrist unit.

SUMMARY

A mechanical wrist unit is designed to be laminated into a prosthetic socket. An adapter has been designed for securing any terminal device with a standard sized threaded stud to the wrist unit. The mechanical wrist unit is designed for full, free rotation of the terminal device secured to the wrist unit, under all realistic load cases, and fine angular specificity at which the rotation can be locked. A combination thrust bearing and tapered bearing enables the free rotation under high load as desired.

Other objects and features will become apparent from the following detailed description considered in conjunction with the accompanying drawings. Drawings are designed to illustrate rather than define the limits of the invention.

BRIEF DESCRIPTION OF THE DRAWINGS

To assist those of skill in the art in making and using the disclosed prosthesis and associated methods, reference is made to the accompanying figures, wherein.

DESCRIPTION

Figure 1:
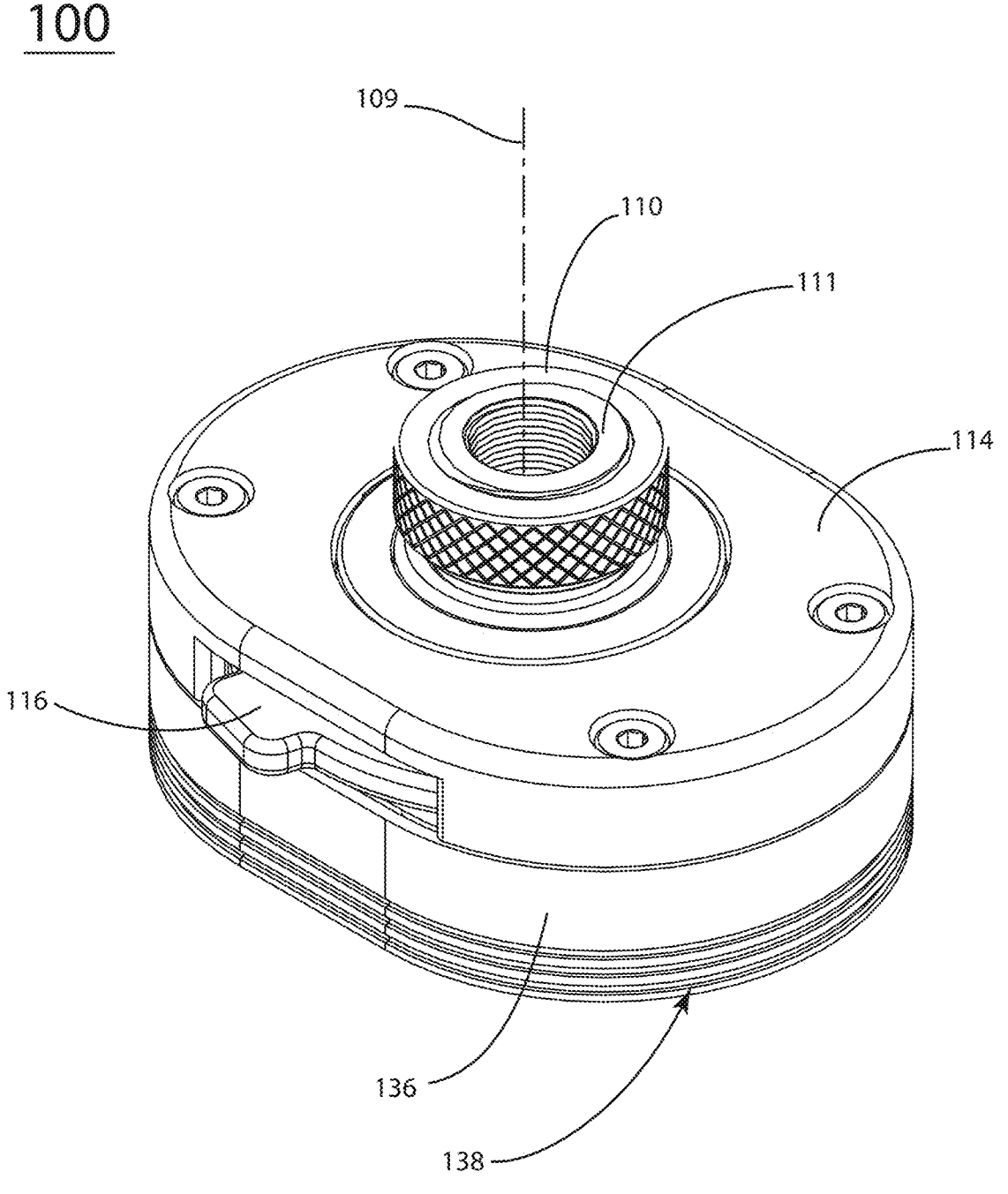
FIG. 1 is a perspective view of an example embodiment.

FIG. 1 shows a wrist unit 100 that is an apparatus for engaging prosthetic-terminal devices which are affixed to an adapter 111 at the distal end of the apparatus. The adapter 111 is held by an adapter collet 110 to components contained within the upper housing 114 and lower housing 136 (FIG. 2) which support bi-directional, axial loading as well as side loading, while rotating the prosthetic about axis 109. A twist ring 116 locks and unlocks the rotation of the adapter 111 so that a prosthetic device threaded into the adapter may rotate freely under load, or may be locked into position while under load. Grooves 138 (FIG. 1), at the proximal end of the apparatus increase adhesion when laminated into a composite prosthetic socket.

Figure 2:
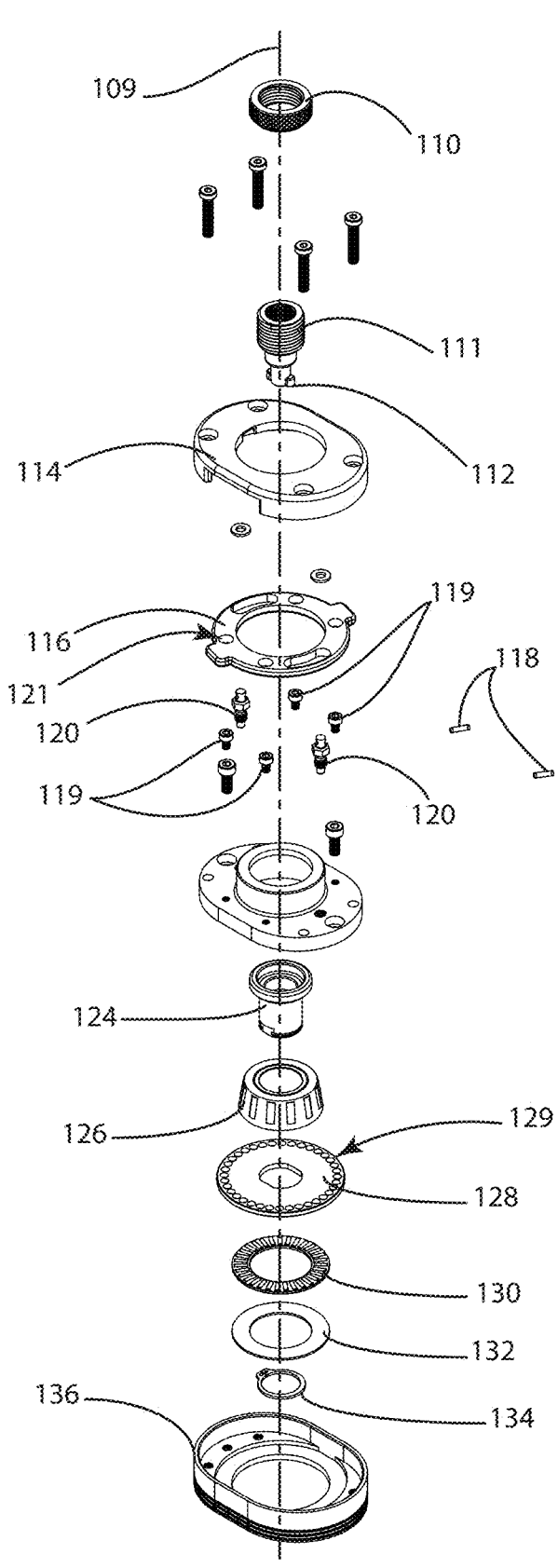
FIG. 2 is an exploded view of the example embodiment of FIG. 1.
Figure 3:
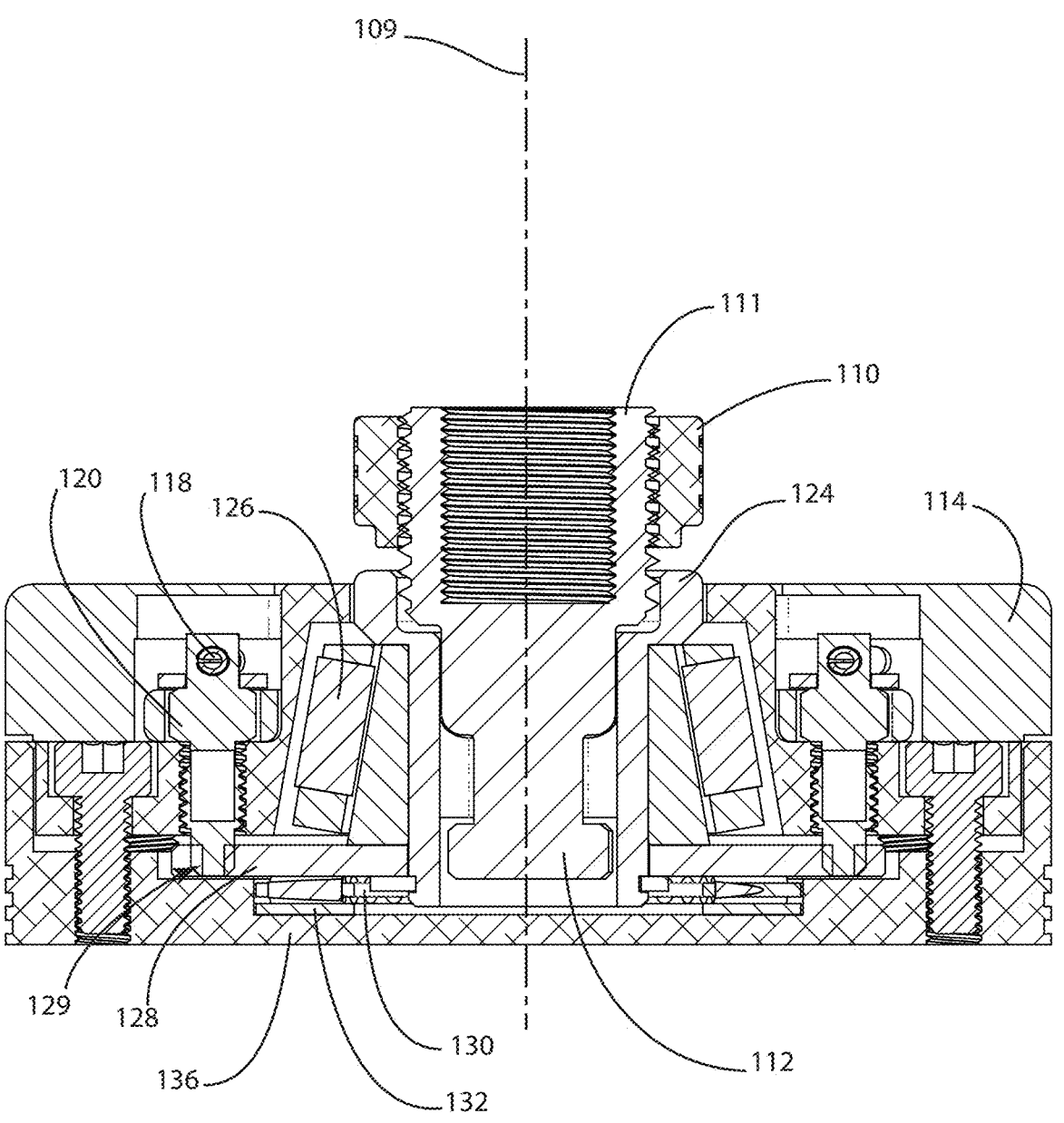
FIG. 3 is a cross-sectional view of the example embodiment of FIG. 1, shown in rotation-locked position.

FIG. 2 shows an exploded view of the wrist unit 100. FIG. 3 shows a cross-sectional view thereof. Referring to FIG. 2 and FIG. 3, an adapter 111 is affixed to a spindle 124 by way of an adapter collet 110. The adapter 111 has a key 112 that engages with a keyway 125 (FIG. 5) in the spindle 124. The adapter collet 110 seats the adapter 111 in the spindle 124 with the key 112 aligned with the keyway 125. An upper housing 114 is affixed by fasteners to a lower housing 136 to contain the components. Spring plungers 120 are affixed to a twist ring 116 by way of roll pins 118. Spring plungers 120 fit into holes 129 in a locking ring gear 128. One skilled in the art is familiar with spring-loaded pins that may be pressed into a hole to provide interference, and are released from the hole by pressure from the spring. Locking spring-loaded pins into the locking ring gear, locks the ring gear in a radial position. Disengaging spring-loaded pins from the locking ring gear allows free rotation. When rotated counterclockwise and pulled upward, the twist ring 116 rests atop fasteners 119. When rotated clockwise, holes 121 in the twist ring 116 align and receive fasteners 119, enabling downward movement of the twist ring as well as downward movement of the spring plungers 120 to fit into holes 129 to lock rotation of the locking ring gear 128 and thus the spindle 124 and a prosthetic engaged therein.

By pulling the twist ring 116 away from the locking ring gear 128, the spring plungers 120 are released from the locking ring gear 128, enabling free rotation of the locking ring gear 128 and spindle 124. Pulling the twist ring distally and twisting the twist ring 116 in a counterclockwise direction enables seating of the twist ring above the twist ring stopper fasteners (119) to put the wrist unit into free-rotation mode. Twisting the twist ring in a clockwise direction allows the spring plungers to pull the twist ring down proximally, enabling re-engagement of the spring plungers 120 with the locking gear 128 to put the wrist unit into rotation-locked mode.

A combination tapered bearing 126 and thrust bearing 130 supports rotation of a prosthetic under load. An adapter 111 is joined to spindle 124 which is in turn joined to the inner race of a tapered bearing 126. The tapered bearing 126 supports loads when the user pulls against the prosthetic or when the prosthetic is under side loading. The thrust bearing supports loads when the user pushes against the prosthetic.

A thrust bearing 130 supports rotation of a prosthetic, which is affixed to the adapter 111, when under axial loading, as when pushing. A thrust bearing washer 132 provides a surface for the thrust bearing 130 to roll against. A retaining ring 134 holds the locking ring gear 128 and the tapered bearing to the spindle 124. One skilled in the art understands how the adapter 111 engaged with the spindle 124 may rotate freely under a load that is carried by the bearing combination.

Figure 4A:
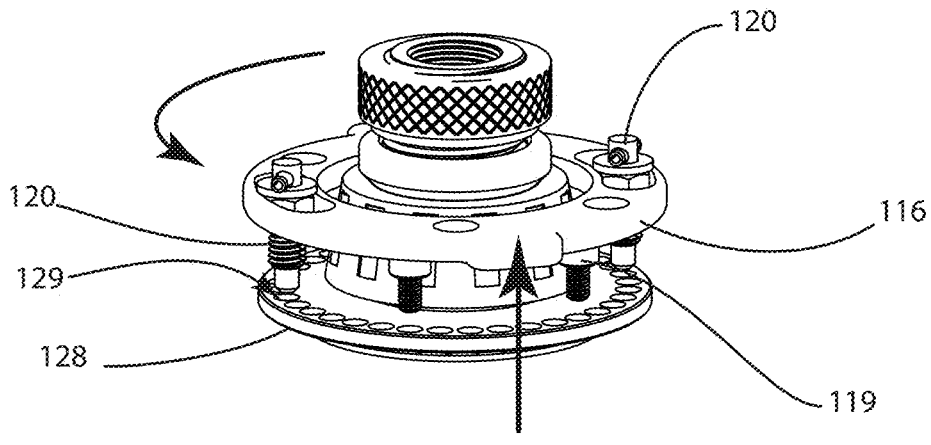
FIG. 4a is a perspective view with some components removed, showing the function of the locking twist ring.
Figure 4B:
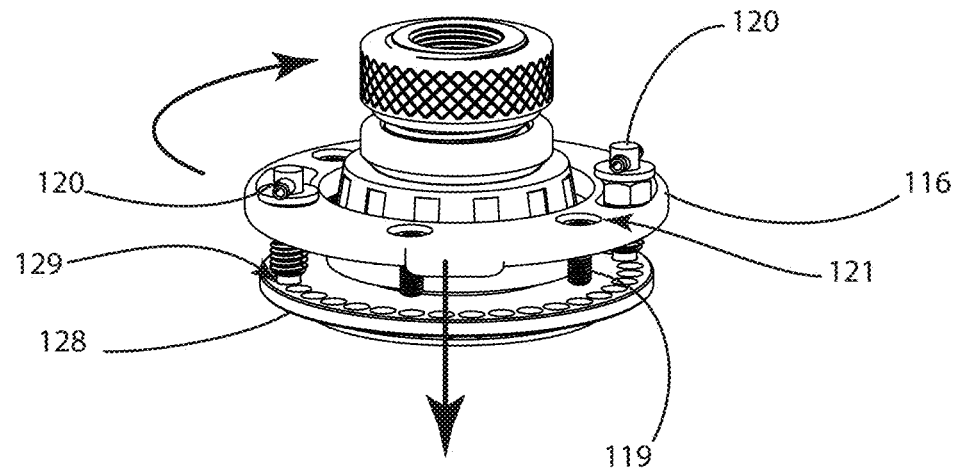
FIG. 4b is another perspective view with some components removed, showing the function of the locking twist ring.

Referring to FIG. 4*a* and FIG. 4*b*: FIG. 4*a* shows a linkage, also referred to as a twist ring 116 with spring plungers 120 disengaged from holes 129 in the locking ring gear 128; and FIG. 4*b* shows a twist ring 116 with spring plungers 120 engaged with holes 129 in the locking ring gear 128. When the twist ring 116 is moved toward the distal end of the apparatus and is rotated counterclockwise as shown in FIG. 4*a*, the twist ring 116 rests on fasteners 119 such that spring plungers 120 are disengaged from holes 129 in the locking ring gear 128. When the twist ring 116 is moved toward the proximal end of the apparatus and is rotated clockwise as shown in FIG. 4*b*, holes 121 align with fasteners 119 such that the twist ring 116 receives fasteners 119. When fasteners 119 are received in the twist ring 116, spring plungers 120 are disengaged from holes 129 in the locking ring gear 128.

Figure 5:
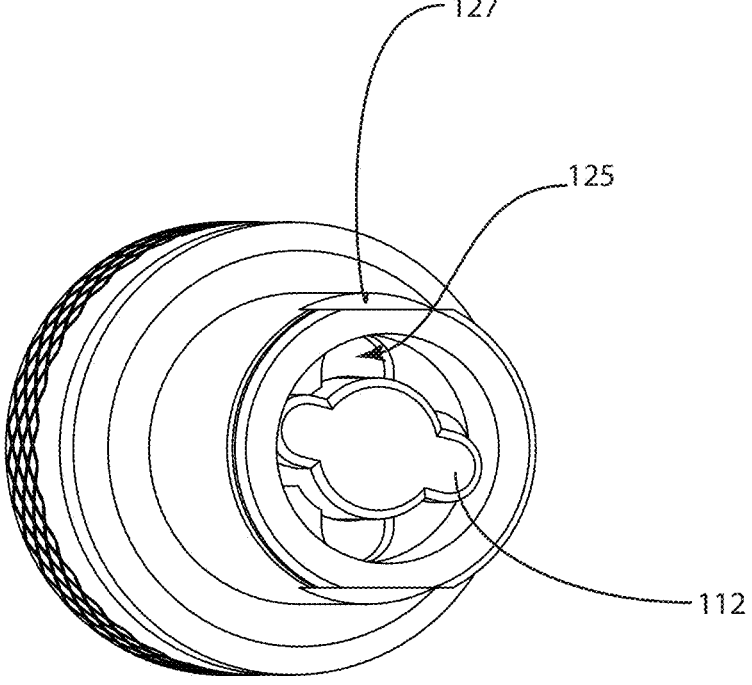
FIG. 5 is a perspective view of an example adapter and spindle.

FIG. 5 shows a detail view of the key 112 engaged in the keyway 125. One skilled in the art is familiar with a key that fits through a hole and twists to cause interference.

These example embodiments should not be construed as limiting.

The invention claimed is:

1. A prosthetic wrist comprising:
a thrust bearing; and
a locking ring gear having a bottom surface and a top surface; and
said thrust bearing rotationally engaged with said bottom surface of said locking ring gear; and
a tapered bearing having an inner race and an outer race, engaged with said top surface of said locking ring gear; and
a spindle rotationally engaged with said tapered-bearing inner race; and
a housing rotationally engaged with said tapered-bearing outer race; and
at least one interference mechanism configured to lock said locking ring gear in a radial position; wherein a prosthetic terminal device fitted into said spindle may be rotated under load while said interference mechanism is not engaged with said locking ring gear, and is held in a fixed radial position when said interference mechanism is engaged with said locking ring gear.

2. The prosthetic wrist of claim 1 further comprising:
at least one spring engaged with said at least one interference mechanism; and
a linkage movably engaged with said interference mechanism, configured to move said interference mechanism against said at least one spring to engage with said locking ring gear; wherein
movement of said linkage in a first direction, allows said at least one spring to elongate and disengage said at least one interference mechanism from said locking ring gear, thus allowing rotation of said spindle under load; and moving said linkage in a second direction compresses said at least one spring, engaging said at least one interference mechanism with said locking ring gear, locking rotation of said spindle.

3. A prosthetic wrist comprising:
a first housing portion rotationally engaged with a thrust bearing; and
a locking ring gear having a bottom surface and a top surface; and
said thrust bearing rotationally engaged with said bottom surface of said locking ring gear; and
a tapered bearing having an inner race and an outer race, engaged with said top surface of said locking ring gear; and
a spindle rotationally engaged with said tapered bearing inner race and fixedly engaged with said locking ring gear; and
a second housing portion rotationally engaged with said tapered bearing outer race; and
said first housing portion and said second housing portion fixedly engaged; and
at least one interference mechanism; and
at least one spring engaged with said at least one interference mechanism; and
a linkage movable in at least a first direction and a second direction, and movably engaged with said interference mechanism, configured to move said interference mechanism against said at least one spring to engage with said locking ring gear; and
an adapter having a receiving end and a keyed end; and
said spindle configured to receive said keyed end of said adapter; and
said adapter receiving end configured to receive a prosthetic hand; wherein
the prosthetic hand fitted into said adapter and said spindle may be rotated under load while said interference mechanism is not engaged with said locking ring gear, and is held in a fixed radial position when said interference mechanism is engaged with said locking ring gear.

* * * * *